(12) United States Patent
Smit et al.

(10) Patent No.: US 10,513,730 B2
(45) Date of Patent: Dec. 24, 2019

(54) ASYMMETRIC PCR METHODS, PRIMERS AND KITS

(71) Applicant: SAFEGUARD BIOSYSTEMS HOLDINGS LTD., London (GB)

(72) Inventors: Nicolaas Smit, Welland (CA); Sonja Bednar, Gundelfingen (DE); Holger Klapproth, Freiburg (DE); Kevin Boynton, Athens, NY (US)

(73) Assignee: Safeguard Biosystems Holdings Ltd., London (GB)

(*) Notice: Subject to any disclaimer, the term of this patent is extended or adjusted under 35 U.S.C. 154(b) by 0 days.

(21) Appl. No.: 15/820,475

(22) Filed: Nov. 22, 2017

(65) Prior Publication Data
US 2019/0153508 A1    May 23, 2019

(51) Int. Cl.
| | | |
|---|---|---|
| *C12Q 1/68* | (2018.01) | |
| *C12Q 1/686* | (2018.01) | |
| *C12Q 1/6848* | (2018.01) | |

(52) U.S. Cl.
CPC ........... *C12Q 1/686* (2013.01); *C12Q 1/6848* (2013.01)

(58) Field of Classification Search
None
See application file for complete search history.

(56) References Cited

U.S. PATENT DOCUMENTS

| | | |
|---|---|---|
| 8,735,067 B2 | 5/2014 | Zhang et al. |
| 2016/0102340 A1* | 4/2016 | Bouzek .............. C12N 15/1003 435/5 |

FOREIGN PATENT DOCUMENTS

| | | |
|---|---|---|
| CN | 104293794 B | 4/2017 |
| EP | 2143805 A1 | 1/2010 |
| WO | 2008/092213 A1 | 8/2008 |

OTHER PUBLICATIONS

Zhu et al. Multiplex Asymmetric PCR-Based Oligonucleotide Microarray for Detection of Drug Resistance Genes Containing Single Mutations in Enterobacteriaceae. Antimicrobial Agents and Chemotherapy 51(10):3707-3713. (Year: 2007).*

(Continued)

*Primary Examiner* — Samuel C Woolwine
(74) *Attorney, Agent, or Firm* — Biospark Intellectual Property Law

(57) ABSTRACT

The disclosure provides an asymmetric PCR amplification method for preparation of single-stranded product and primers and kits useful therefor.

29 Claims, 11 Drawing Sheets

Specification includes a Sequence Listing.

ASYMMETRIC PRIMER PAIR

Extended Primer

Unextended Primer

(56) References Cited

OTHER PUBLICATIONS

Mazars et al. Direct sequencing by thermal asymmetric PCR. Nucleic Acids Research 19(17):4783. (Year: 1991).*

Kaboev et al. PCR hot start using primers with the structure of molecular beacons (hairpin-like structure). Nucleic Acids Research 28(21):e94. (Year: 2000).*

Pierce et al., 2005, "Linear-After-The-Exponential (LATE)-PCR: Primer design criteria for high yields of specific single-stranded DNA and improved real-time detection," PNAS 102(24):8609-8614.

Sanchez et al., 2004, "Linear-After-The-Exponential (LATE)-PCR: An advanced method of asymmetric PCR and its uses in quantitative real-time analysis," PNAS 101(7):1933-1938.

Zhu et al., 2007, "Multiplex Asymmetric PCR-Based Oligonucleotide Microarray for Detection of Drug Resistance Genes Containing Single Mutations in *Enterobacteriaceae*," Antimicrobial Agents and Chemotherapy 51(10):3707-3713.

Notification of Transmittal of the International Search Report and Written Opinion of the International Searching Authority, or the Declaration, International Search Report, and Written Opinion of the International Searching Authority, dated Feb. 12, 2019 in PCT/EP2018/082086.

\* cited by examiner

Denaturation

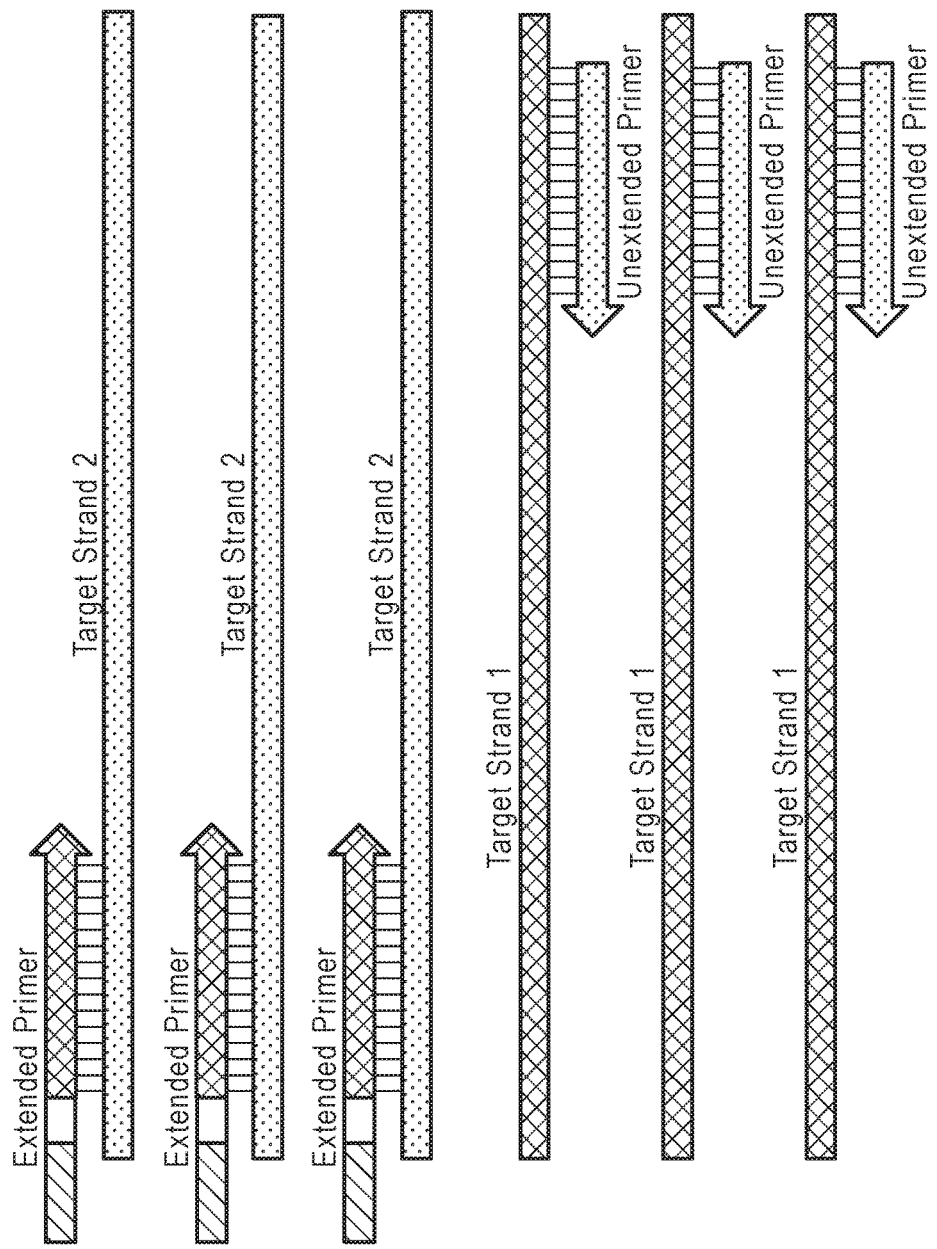

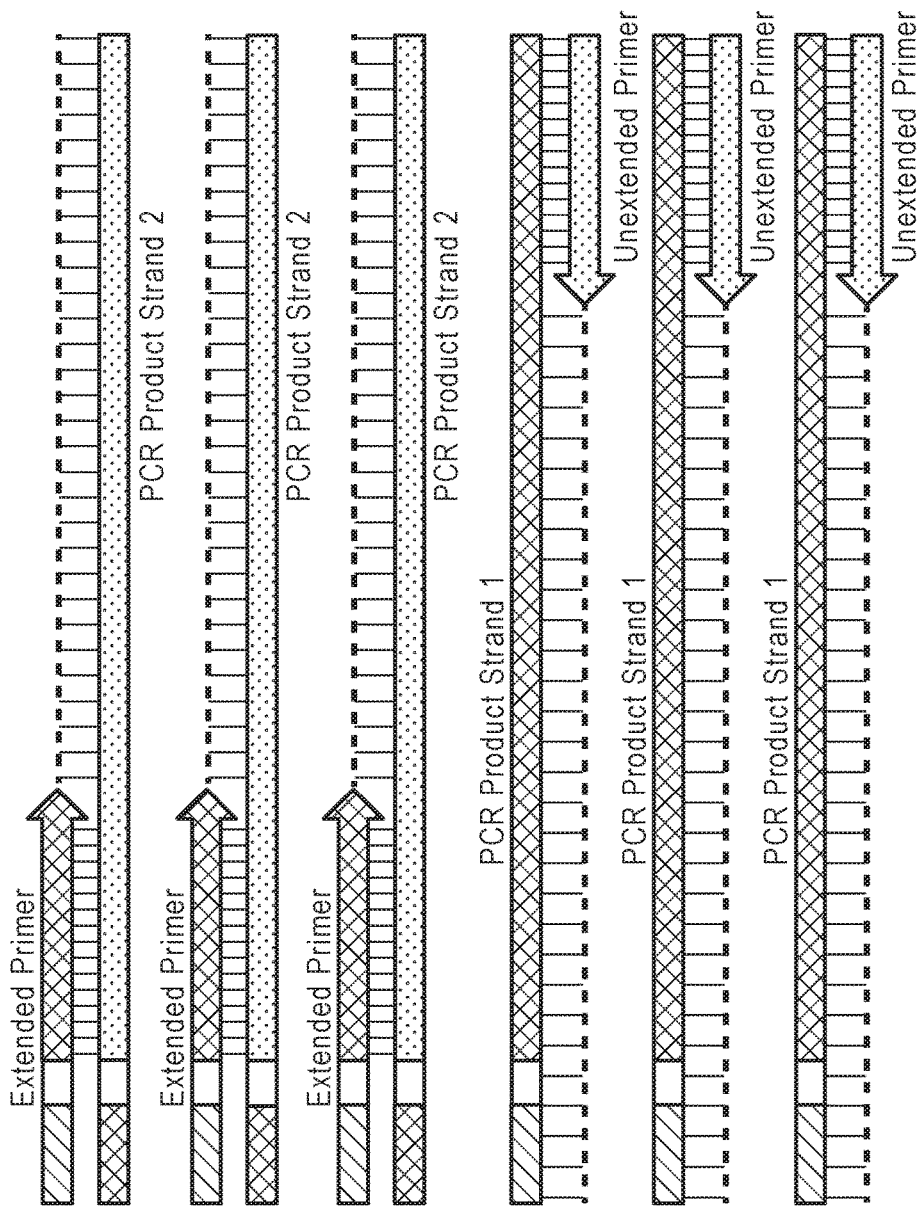

```
TACCTGGTTGATCCTGCCAGTAGTCATATGCTTGTCTCAAAGATTAAGCCATGCATGTGTAAGTATGAAC
AAATTCAGACTGTGAAACTGCTGAATGCTCATTAAATCAGTTATAGTTTGTTTGATGGTATCTCTACTC
GGATAACCCGTAGTAATTCTAGAGCTAATACGTGCAACAAACCCGACTTCTGGAAGGGATGCATTTATTA
GATAAAAGGTCGACGCGGGCTCTGCTGCTGCGATGATTCATGATAATCGACGGATCGCACGGCCATCGT
GCCGGCGACGCATTCAAATTTCTGCCTATCAACTTTCTGATGGTAGGATAGTGGCCTACCATGGTGG
TGACGGGTGACGGAGAATTAGGGTTCGATTCCGGAGAGGGAGCCTGAGAAACGGCTACCACATCCAAGGA
AGGCAGCAGGCGCGCAAATTACCCAATCCTGACACGGGGAGGTAGTGACAATAATAACAATACCGGGCT
CTATGAGTCTGGTAATGGAATGAGTACAATCTAAATCCCTTAAGGATCCATTGGAGGCAAGTCTG
GTGCCAGCAGCCGCGGTAATTCAGCTCCGGGTCCGCCCGCGGTATATTTAAGTTGTTGCAGTTAAAAGCTCGTAG
TTGGACTTTGGGATGGCCCGGTTAATTGGCCGGATAACATTAAGTTGTGCACCGGTCTCGTCCCTTCTGTCGGCGA
TGCCGCTCCTGCCTTAATTGGCCGGTCGTGCCGGTGTTACTTGAAGAAATTAGAGTGCTCAA
AGCAAGCCTACGCTCTGTATACATTAGCATGGGATAAACATTATAGGATTTCGGTCCTATTACGTTGGCCT
TCGGGATCGAGTAATGATTAACAGGGACAGTCGGGGCATTCGTATTTCGTATTTCATAGTCAGAGGTGAAATTCT
TGGATTTATGAAAGACGAACAACTGCGAAAGCATTTGCCAAGGATGTTTTCATTAATCAAGAACGAAAGT
TGGGGGCTCGAAGACGATCAGATACCGTCCTAGTCTCAACCATAAACGATGCCAACCAGGATCGGCGGA
TGTTGCTTTTAGGACTCCGCCCGCACTTAAAAGGAATTGACGGAAGGGCACCACCAGGAGTGGAGCCTGCGGCTTAATTTGACT
GCAAGGCTGAAACTTAAAGGAATTGACGGAAGGGCACCACCAGGAGTGGAGCCTGCGGCTTAATTTGACT
CAACACGGGGAAACTTACCAGGTCCAGATCAGTAGTAGGATTGACAGACTGAGAGCTCTTTCTTGATTCTA
TGGGTGGTGGTGCATGGCCGTTCTTAGTTGCGGAGCGATTTGTCTCGGTTAATTCCGTTAACGAACGAGA
CCTCAGCCCTGCTAACTAGCTATGCGGAGGTATCCCTTCGCGCCAGCTTCTTAGAGGGACTAGCCTTTA
GGCCGCGGAAGTTTGAGGCAATAACAGGTCTGTGATGCCCTTAGATGTTCTGGGCCCACCGCGCTACAC
TGATGTATTCAACGAGCTTATAGCCTTGCGACAGGCGGAATTCCTCAACGAGGAATTCCTCTAGTAAGCGCGAGTCATCAGCTCGTGATGGG
ATAGATCATTGCAATTGTTGGTCTTCAACACCGCCCGTCGCTCCTACCGATTGAAGATCCGGTGAAATGTTCGGAT
TACGTCCCTGCCTTTGTACACACCGCCCGTCGCTCCTACCGATTGAAGATCCGGTGAAATGTTCGGAT
CGCGGCGACGTGGCGGTTCGCTGCCCGCGACGTCGCGAGAAGTCCATTGAACCTTATCATTTAGAGGAA
GGAGAAGTCGTAACAAGGTTTCCGTAGGTGAACCTGCGGAAGGATCATT
```

FIG. 7A

Extended forward primer

CAT CAA ACA TG TTT GAT GGT ATC TAC TAC TCG GAT AAC CG

Unextended reverse primer

GCG ATC CGT CGA GTT ATC ATG AAT C

FIG. 7B

SEQUENCE LISTING

```
<160> NUMBER OF SEQ ID NOS: 3

<210> SEQ ID NO 1
<211> LENGTH: 1799
<212> TYPE: DNA
<213> ORGANISM: Solanum lycopersicum

<400> SEQUENCE: 1
tacctggttg atcctgccag tagtcatatg cttgtctcaa agattaagcc atgcatgtgt      60
aagtatgaac aaattcagac tgtgaaactg cgaatggctc attaaatcag ttatagtttg     120
tttgatggta tctactactc ggataaccgt agtaattcta gagctaatac gtgcaacaaa     180
ccccgacttc tggaagggat gcatttatta gataaaaggt cgacgcgggc tctgctgctg     240
cgatgattca tgataactcg acggatcgca cggccatcgt gccggcgacg catcattcaa     300
atttctgccc tatcaacttt cgatggtagg atagtggcct accatggtgg tgacgggtga     360
cggagaatta gggttcgatt ccggagaggg agcctgagaa acggctacca catccaagga     420
aggcagcagg cgcgcaaatt acccaatcct gacacgggga ggtagtgaca ataaataaca     480
ataccgggct ctatgagtct ggtaattgga atgagtacaa tctaaatccc ttaacgagga     540
tccattggag ggcaagtctg gtgccagcag ccgcggtaat tccagctcca atagcgtata     600
tttaagttgt tgcagttaaa aagctcgtag ttggactttg ggatgggccg gccggtccgc     660
cctaggtgtg caccggtcgt ctcgtccctt ctgtcggcga tgcgctcctg gccttaattg     720
gccgggtcgt gcctccggcg ctgttacttt gaagaaatta gagtgctcaa agcaagccta     780
cgctctgtat acattagcat gggataacat tataggattt cggtcctatt acgttggcct     840
tcgggatcgg agtaatgatt aacagggaca gtcgggggca ttcgtatttc atagtcagag     900
gtgaaattct tggatttatg aaagacgaac aactgcgaaa gcatttgcca aggatgtttt     960
cattaatcaa gaacgaaagt tgggggctcg aagacgatca gataccgtcc tagtctcaac    1020
cataaacgat gccgaccagg gatcggcgga tgttgctttt aggactccgc cggcaccta    1080
```

```
tgagaaatca aagttttgg gttccggggg gagtatggtc gcaaggctga aacttaaagg    1140
aattgacgga agggcaccac caggagtgga gcctgcggct taatttgact caacacgggg    1200
aaacttacca ggtccagaca tagtaaggat tgacagactg agagctcttt cttgattcta    1260
tgggtggtgg tgcatggccg ttcttagttg gtggagcgat ttgtctggtt aattccgtta    1320
acgaacgaga cctcagcctg ctaactagct atgcggaggt atcccttcgc ggccagcttc    1380
ttagagggac tagccttta ggccgcggaa gtttgaggca ataacaggtc tgtgatgccc    1440
ttagatgttc tgggcccacg cgcgctacac tgatgtattc aacgagctta tagccttgcc    1500
gacaggcccg ggtaatcttt gaaatttcat cgtgatgggg atagatcatt gcaattgttg    1560
gtcttcaacg aggaattcct agtaagcgcg agtcatcagc tcgcgttgac tacgtccctg    1620
ccctttgtac acaccgcccg tcgctcctac cgattgaatg atccggtgaa atgttcggat    1680
cgcggcgacg tgggcggttc gctgcccgcg acgtcgcgag aagtccattg aaccttatca    1740
tttagaggaa ggagaagtcg taacaaggtt tccgtaggtg aacctgcgga aggatcatt    1799
```

<210> SEQ ID NO 2
<211> LENGTH: 40
<212> TYPE: DNA
<213> ORGANISM: artificial sequence
<220> FEATURE:
<223> OTHER INFORMATION: Extended forward primer

<400> SEQUENCE: 2

```
catcaaacat gtttgatggt atctactact cggataaccg                           40
```

<210> SEQ ID NO 3
<211> LENGTH: 25
<212> TYPE: DNA
<213> ORGANISM: artificial sequence
<220> FEATURE:
<223> OTHER INFORMATION: Unextended reverse primer

<400> SEQUENCE: 3

```
gcgatccgtc gagttatcat gaatc                                           25
```

ASYMMETRIC PCR METHODS, PRIMERS AND KITS

The instant application contains a Sequence Listing which has been submitted electronically in ASCII format and is hereby incorporated by reference in its entirety. Said ASCII copy, created on Jan. 11, 2018 is named 180112_SGB-004US_Sequence_Listing_ACK and is 3,058 bytes in size.

1. BACKGROUND

The polymerase chain reaction (PCR) is widely used to amplify stretches of DNA, including genomic DNA as well as cDNA reverse transcribed from RNA, for assays for diagnostic and other purposes. PCR is a repeated series of steps of denaturation, or strand melting, to create single-stranded templates; primer annealing; and primer extension by a thermally stable DNA polymerase such as *Thermus aquaticus* (Taq) DNA polymerase.

A typical three-step PCR protocol (see PCR PROTOCOLS, a Guide to Methods and Applications, Innis et al. eds., Academic Press (San Diego, Calif. (USA) 1990, Chapter 1) may include denaturation, or strand melting, at 93-95° C. for more than 5 sec, primer annealing at 55-65° C. for 10-60 sec, and primer extension for 15-120 sec ata temperature at which the polymerase is highly active, for example, 72° C. for Taq DNA polymerase. A typical two-step PCR protocol may differ by having the same temperature for primer annealing as for primer extension, for example, 60° C. or 72° C. For either three-step PCR or two-step PCR, amplification involves cycling the reaction mixture through the foregoing series of steps numerous times, typically 25-40 times. During the course of the reaction the times and temperatures of individual steps in the reaction may remain unchanged from cycle to cycle, or they may be changed at one or more points in the course of the reaction to promote efficiency or enhance selectivity.

In addition to the pair of primers and target nucleic acid a PCR reaction mixture typically contains each of the four deoxyribonucleotide 5' triphosphates (dNTPs), typically at equimolar concentrations, a thermostable polymerase, a divalent cation (typically $Mg^{2+}$), and a buffering agent. A reverse transcriptase is typically included for RNA targets, unless the polymerase possesses that activity. The volume of such reactions is typically 25-100 μl. Multiple target sequences can be amplified in the same reaction. In the case of cDNA amplification, PCR is preceded by a separate reaction for reverse transcription of RNA into cDNA, unless the polymerase used in the PCR possesses reverse transcriptase activity. The number of cycles for a particular PCR amplification depends on several factors including: a) the amount of the starting material, b) the efficiency of the reaction, and c) the method and sensitivity of detection or subsequent analysis of the product. Cycling conditions, reagent concentrations, primer design, and appropriate apparatuses for typical cyclic amplification reactions are well known in the art (see, for example, Ausubel, F. Current Protocols in Molecular Biology (1988) Chapter 15: "The Polymerase Chain Reaction," J. Wiley (New York, N.Y. (USA)).

Ideally, each strand of each amplicon molecule hybridizes to (referred to as "binding" to) a primer at one end and serves as a template for a subsequent round of synthesis. The rate of generation of primer extension products, or amplicons, is thus exponential, doubling during each cycle. The amplicons include both plus (+) and minus (−) strands, which hybridize to one another to form double strands.

PCR reactions are typically designed to be symmetric, that is, to make double-stranded copies by utilizing a forward primer and a reverse primer designed to have "melting temperatures," or "$T_m$'s" that equal or within a few ° C. of one another. Commonly used computer software programs for primer design warns users to avoid high $T_m$ difference, and have automatic $T_m$ matching features.

To differentiate typical PCR from the asymmetric PCR methods described herein, typical PCR is referred to herein as "symmetric" PCR. Symmetric PCR thus results in an exponential increase of one or more double-stranded amplicon molecules, and both strands of each amplicon accumulate in equal amounts during each round of replication. The efficiency of exponential amplification via symmetric PCR eventually declines, and the rate of amplicon accumulation slows down and stops. Kinetic analysis of symmetric PCR reveals that reactions are composed of a) an undetected amplification phase (initial cycles) during which both strands of the target sequence increase exponentially, but the amount of the product thus far accumulated is below the detectable level for the particular method of detection in use; b) a detected amplification phase (additional cycles) during which both strands of the target sequence continue to increase in parallel and the amount of the product is detectable; c) a plateau phase (terminal cycles) during which synthesis of both strands of the amplicon gradually stops and the amount of product no longer increases. Symmetric reactions slow down and stop because the increasing concentrations of complementary amplicon strands hybridize to each other (reanneal), and this out-competes the ability of the separate primers to hybridize to their respective target strands. Typically reactions are run long enough to guarantee accumulation of a detectable amount of product, without regard to the exact number of cycles needed to accomplish that purpose.

A technique that has found limited use for making single-stranded DNA directly in a PCR reaction is "asymmetric PCR." Gyllensten and Erlich, 1988, Proc. Natl. Acad. Sci. (USA) 85: 7652-7656 (1988); Gyllensten and Erlich, 1991, U.S. Pat. No. 5,066,584. Traditional asymmetric PCR differs from symmetric PCR in that one of the primers is added in limiting amount, typically $1/100^{th}$ to $1/5^{th}$ of the concentration of the other primer. Double-stranded amplicon accumulates during the early temperature cycles, as in symmetric PCR, but one primer is depleted, typically after 15-25 PCR cycles, depending on the number of starting templates. Linear amplification of one strand takes place during subsequent cycles utilizing the undepleted primer. Primers used in asymmetric PCR reactions reported in the literature are often the same primers known for use in symmetric PCR. Poddar (Poddar, 2000, Mol. Cell Probes 14: 25-32) compared symmetric and asymmetric PCR for amplifying an adenovirus substrate by an end-point assay that included 40 thermal cycles. He reported that a primers ratio of 50:1 was optimal and that asymmetric PCR assays had better sensitivity that, however, dropped significantly for dilute substrate solutions that presumably contained lower numbers of target molecules.

Thus, there is a need for improved asymmetric PCR amplification methods that are capable of detecting target molecules present in low quantities in a sample, for example in diagnostic applications.

2. SUMMARY

The present disclosure relates to improved asymmetric PCR methods and primers and kits useful therefor.

The asymmetric PCR methods of the disclosure include both an exponential phase and a linear phase. During the exponential phase, both strands of the target nucleic acid are amplified. During the linear phase, only one of the strands is amplified, resulting in an excess of a single strand of target nucleic acid.

The asymmetric PCR methods achieve the excess of a single strand though the use of primer pairs of different lengths and melting temperatures, with the longer primer referred to herein as the "Extended Primer" and the shorter primer referred to herein as the "Unextended Primer". The Extended Primer has a higher melting temperature than the Unextended Primer and can be used to selectively amplify a single strand of the target nucleic acid using PCR cycles in which the annealing step is performed at a temperature greater than the melting temperature of the Unextended Primer but lower than the melting temperature of the Extended Primer. The selective amplification gives rise to a PCR product mixture that is enriched in the target strand to be probed in a subsequent detection assay.

The Extended Primers contain in addition to the sequence complementary to the target nucleic acid a 5' extension containing a sequence that is complementary to the target-binding portion of the same primer. Without being bound by theory, the inventors believe that the use of the 5' extension allows intra- or inter-molecular hybridization of Extended Primer molecules and prevents arbitrary or non-specific binding of these longer primers to DNA molecules present in the PCR reaction at the beginning of the PCR reaction. This in turns prevents non-specific DNA amplification and prevents "noise" in the PCR product, which can be problematic when amplifying a target that is present in low quantities in a biological sample.

Another aspect of this disclosure is reagent kits for performing the asymmetric PCR procedures described herein.

3. BRIEF DESCRIPTION OF THE FIGURES

FIG. 1: illustrates a primer pair useful for the asymmetric PCR methods of the disclosure, comprising an Unextended Primer which can be a traditional primer used in symmetric PCR processes and an Extended Primer composed of an "A" region, which is complementary to the target nucleic acid, a "B" region which includes a Direct Repeat or Inverted Repeat of at least a portion of the "A" region, and an optional "C" region, which can include a spacer sequence and/or part of all of a restriction endonuclease recognition site.

FIG. 2A-2C. FIG. 2A illustrates intermolecular hybridization of Extended Primers that occurs when the "B" region contains an Inverted Repeat of at least a portion of the "A" region. FIG. 2B illustrates intermolecular hybridization of Extended Primers that occurs when the "B" region contains a Direct Repeat of at least a portion of the "A" region. FIG. 2C illustrates intramolecular hybridization of Extended Primers that occurs when the "B" region contains an Inverted Repeat of at least a portion of the "A" region. Preferably, the region of complementarity between the "A" region and the "B" region is at or near the 5' end of the "A" region.

FIG. 3 illustrates the denaturation step in an asymmetric PCR reaction of the disclosure. In the denaturation step a PCR reaction mixture (typically containing a biological sample containing or at risk of containing target nucleic acid, an Asymmetric Primer Pair, a thermostable DNA polymerase, and PCR Reagents) is heated to above the melting point of the target nucleic acid, resulting in denaturation of the target nucleic acid (if present) and the Extended Primer in the Asymmetric Primer Pair so as to form single strands.

FIG. 4 illustrates the annealing step of the exponential phase of the asymmetric PCR reactions of the disclosure, which occurs below the melting temperature of the Unextended Primer. Both the Unextended Primer and Extended Primer in the Asymmetric Primer Pair hybridize to their respective complementary strands. FIG. 4 shows annealing (also referred to as hybridization or binding) to target DNA, as occurs in the initial cycles of PCR, but in subsequent cycles annealing is likely to occur between primers and complementary sequences in PCR products. Because of the "B" and optional "C" regions in the Extended Primer, the PCR products will have those sequences or their complements, as depicted in FIG. 5B and FIG. 6.

FIGS. 5A-5B: FIG. 5A and FIG. 5B illustrate the extension step of the exponential phase of the asymmetric PCR reactions of the disclosure, during which the thermostable DNA polymerase extends the primer DNA using the complementary DNA as template. The region of extension is depicted in dashed lines. The template in FIG. 5A is a strand of target DNA, and in FIG. 5B is a strand of PCR product produced using the Asymmetric Primer Pair and the target DNA.

FIG. 6 illustrates the simultaneous annealing and extension step of the linear phase of the asymmetric PCR reactions of the disclosure, which occurs above the melting temperature of the Unextended Primer and below the melting temperature of the Extended Primer, using the PCR Product Strand 2 as template. This results in asymmetric amplification of PCR Product Strand 2, resulting in an excess of PCR Product Strand 2 molecules relative to PCR Product Strand 1 molecules by the end of the PCR reaction.

FIG. 7A-7B: FIG. 7A shows the *Solanum lycopersicum* 17S ribosomal RNA sequence (SEQ ID NO:1), with a 160-base target region shown in bold that is amplified using the Asymmetric Primer Pair shown in FIG. 7B. FIG. 7B shows an Asymmetric Primer Pair (SEQ ID NO:2 and SEQ ID NO:3) useful for amplification of the 160-base region shown in bold in FIG. 7A, with the "A" region of the Extended Primer shown in regular text and the "B" region (which is an Inverted Repeat of the double underlined portion of the "A" region) shown in bold text. This Extended Primer does not contain the optional "C" region.

4. DETAILED DESCRIPTION

4.1. Definitions

Figure 1:
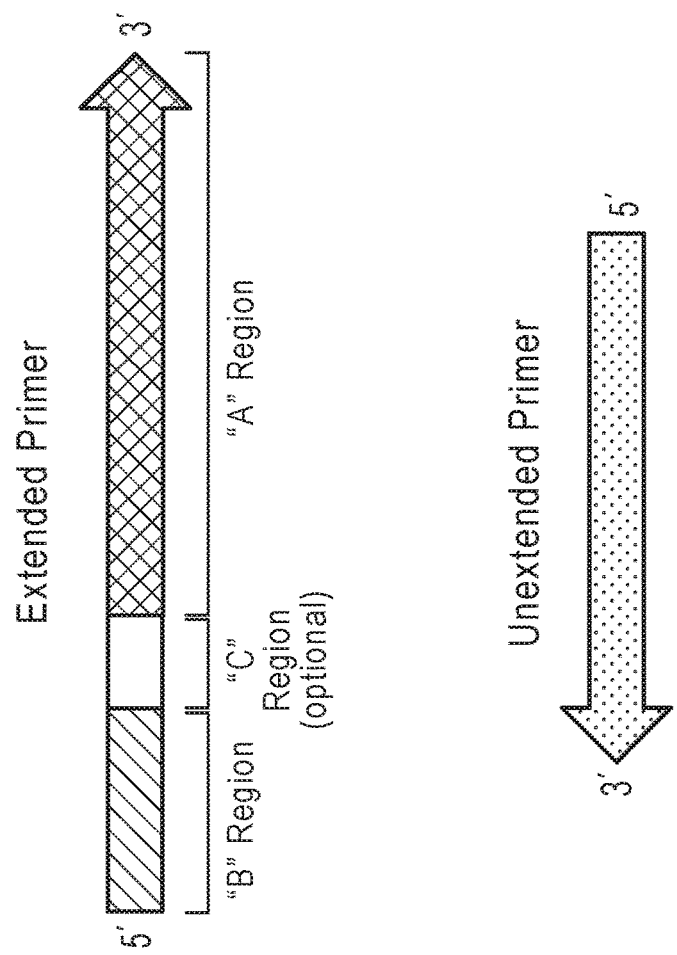

Extended Primer: A PCR primer that contains (a) an "A" region at its 3' end that has at least 75% sequence identity to a corresponding region Target Strand 1 or at least 75% sequence complementarity to a corresponding region in Target Strand 2; (b) a "B" region at its 5' end that comprises a sequence that is complementary to at least a portion of the "A" region; and (c) an optional "C" region positioned between the "A" and "B" regions.

Unextended Primer: A PCR primer that consists essentially of a nucleotide sequence having at least 75% sequence identity to a corresponding region in Target Strand 2 or at least 75% sequence complementarity to a corresponding region in Target Strand 1. The term "consisting essentially of" in reference to the Unextended Primer means that the nucleotide sequence may contain no more than 3 additional nucleotides 5' to the region of (at least 75%) complementarity to the target sequence.

Primer Pair: A forward and reverse primer pair (each of which can be a mixture of primers with sequence variations to account for possible variations in the target sequence) that is capable of hybridizing with and initiating a DNA polymerization reaction from different strands of the same nucleic acid molecule within a region of less than 5,000 base pairs. In certain embodiments, the primer pair is capable of hybridizing with an initiating a DNA polymerization reaction from different strands of the same nucleic acid molecule within a region of less than 2,500 base pairs or less than 1,500 base pairs.

Asymmetric Primer Pair: A Primer Pair consisting of an Extended Primer and an Unextended Primer.

Melting temperature ($T_m$): the temperature at which a one half of a DNA duplex will dissociate to become single stranded. The $T_m$'s of linear primers comprised of deoxyribonucleotides (DNA) have been commonly calculated by the "percent GC" method (PCR PROTOCOLS, a Guide to Methods and Applications, Innis et al. eds., Academic Press (San Diego, Calif. (USA) 1990) or the "2 (A+T) plus 4 (G+C)" method (Wallace et al., 1979, Nucleic Acids Res. 6 (11):3543-3557) or the "Nearest Neighbor" method (Santa Lucia, 1998, Proc. Natl. Acad. Sci. USA 95: 1460-1465; Allawi and Santa Lucia, 1997, Biochem. 36:10581-10594). For the purpose of the claims, the $T_m$ of a DNA is calculated according to the "Nearest Neighbor" method, and non-naturally occurring bases (e.g., 2-deoxyinosine) are treated as adenines.

Primer: A DNA oligonucleotide of at least 12 nucleotides that has a free hydroxyl group at its 3' terminus. Primers can include naturally and non-naturally occurring nucleotides (e.g., nucleotides containing universal bases such as 3-nitropyrrole, 5-nitroindole or 2-deoxyinosine, 2-deoxyinosine being preferred). Unless the context dictates otherwise, the term "primer" also refers to a mixture of primer molecules that is created when mixed bases are included in the primer design and construction to allow them to hybridize to variant sequences in the target nucleic acid molecules. The target sequence variants can be inter- or intra-species variants. Standard nomenclature for mixed bases is shown in Table 1:

TABLE 1

| Mixed Base Nomenclature | |
|---|---|
| R | A, G |
| Y | C, T |
| M | A, C |
| K | G, T |
| S | C, G |
| W | A, T |
| H | A, C, T |
| B | C, G, T |
| V | A, C, G |
| D | A, G, T |
| N | A, C, G, T |

Preferably, each primer contains no more than three mixed bases in the region of complementarity to the target nucleic acid. In some embodiments, a primer contains zero, one, two or three mixed bases in the region of complementarity to the target nucleic acid.

Generic Primer: A primer whose sequence consists essentially of the "B" region of the Extended Primer. Preferably, the asymmetric DNA amplification methods of the disclosure are performed in the absence of Generic Primers.

Direct Repeat: In the context of the "B" region of an Extended Primer, "Direct Repeat" means a nucleotide sequence that is the direct complement to a portion of the "A" region (i.e., has the complementary sequence in the same 5' to 3' order).

Inverted Repeat: In the context of the "B" region of an Extended Primer, "Inverted Repeat" means a nucleotide sequence that is the reverse complement to a portion of the "A" region (i.e., has the complementary sequence in the opposite 5' to 3' order).

PCR Reagents: unless the context dictates otherwise, the term "PCR Reagents" refers to components of a PCR reaction other than template nucleic acid, thermostable polymerase and primers. PCR Reagents typically include dNTPs (and may include labeled, e.g., fluorescently labeled, dNTPs in addition to unlabeled dNTPs), buffers, and salts containing divalent cations (e.g., $MgCl_2$).

Target Strand 1: Target Strand 1 refers to the strand in a double-stranded target nucleic acid to which an Unextended Primer in an Asymmetric Primer Pair is complementary.

Target Strand 2: Target Strand 2 refers to the strand in a double-stranded target nucleic acid to which the "A" region in an Extended Primer in an Asymmetric Primer Pair is complementary.

PCR Product Strand 1: PCR Product Strand 1 refers to the strand in a double-stranded PCR product produced from target nucleic acid and an Asymmetric Primer Pair which is complementary to the Unextended Primer of the Asymmetric Primer Pair.

PCR Product Strand 2: PCR Product Strand 1 refers to the strand in a double-stranded PCR product produced from target nucleic acid and an Asymmetric Primer Pair which is complementary to the Extended Primer of the Asymmetric Primer Pair.

Corresponding: In relation to two nucleic acid strands of different length that share sequence identity or complementary, the term "corresponding" refers to the region of sequence overlap or complementarity present in both strands, as the context dictates.

Approximately: In reference to an integer, the term "approximately" expands the integer to include the fractional values up to 0.50 lower and up to 0.49 higher. For example, a temperature of "approximately 68° C." means a temperature of 67.50° C.-68.49° C. and a sequence identity of "approximately 95%" means a percent sequence identity of 94.50%-95.49%.

About: When used in a quantitative context, the term "about" should be construed as to include up to 10% above the stated value and down to minus 10% of the stated value. In the context of a range, the term "about" should be construed to include values of up to 10% above the upper limit and down to 10% below the lower limit of the stated range.

Nucleic Acid Sample: Means a sample that may be a source of target nucleic acid or a dummy sample used as a negative control containing non-target nucleic acid or no nucleic acid (for example, to measure or detect contamination or non-specific amplification). The nucleic acid sample does not necessarily contain target DNA, for example in the case of a diagnostic sample, the sample might be a biological sample suspected or at risk of containing a target nucleic acid, for example as described in Section 4.3

4.2. Primer Design

4.2.1. Extended Primer

The "A" region of the Extended Primer has at least 75% sequence identity to a corresponding region in Target Strand 1. In certain embodiments, the "A" region of the primer has at least 80%, at least 85%, at least 90%, or at least 95% identical to the corresponding region in Target Strand 1. In yet other embodiments, the "A" region of the primer has 100% sequence identity to the corresponding region of Target Strand 1.

Stated differently, in various embodiments the "A" region of the Extended Primer has at least 75%, at least 80%, at least 85%, at least 90%, or at least 95% or 100% sequence identity to the complement of the corresponding region in Target Strand 2. Typically, the more 5' any mismatches are between the primer sequence and the target sequence are positioned, the more likely they are to be tolerated during the PCR reaction. One of skill in the art can readily design primer sequences that have less than 100% sequence identity to the target strand but can still efficiently amplify target DNA.

Figure 2A:
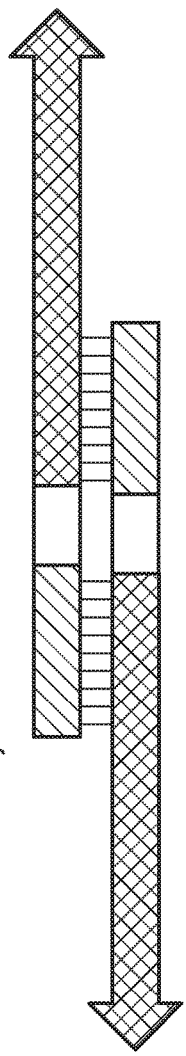
Figure 2B:
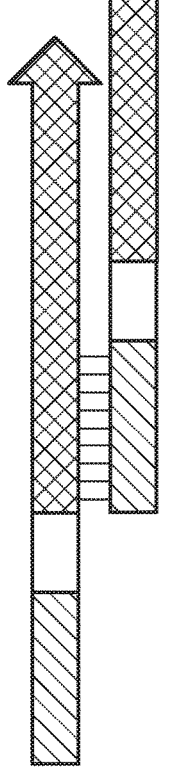
Figure 2C:
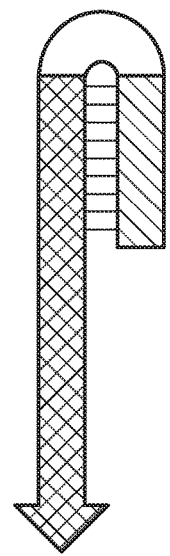
Figure 3:
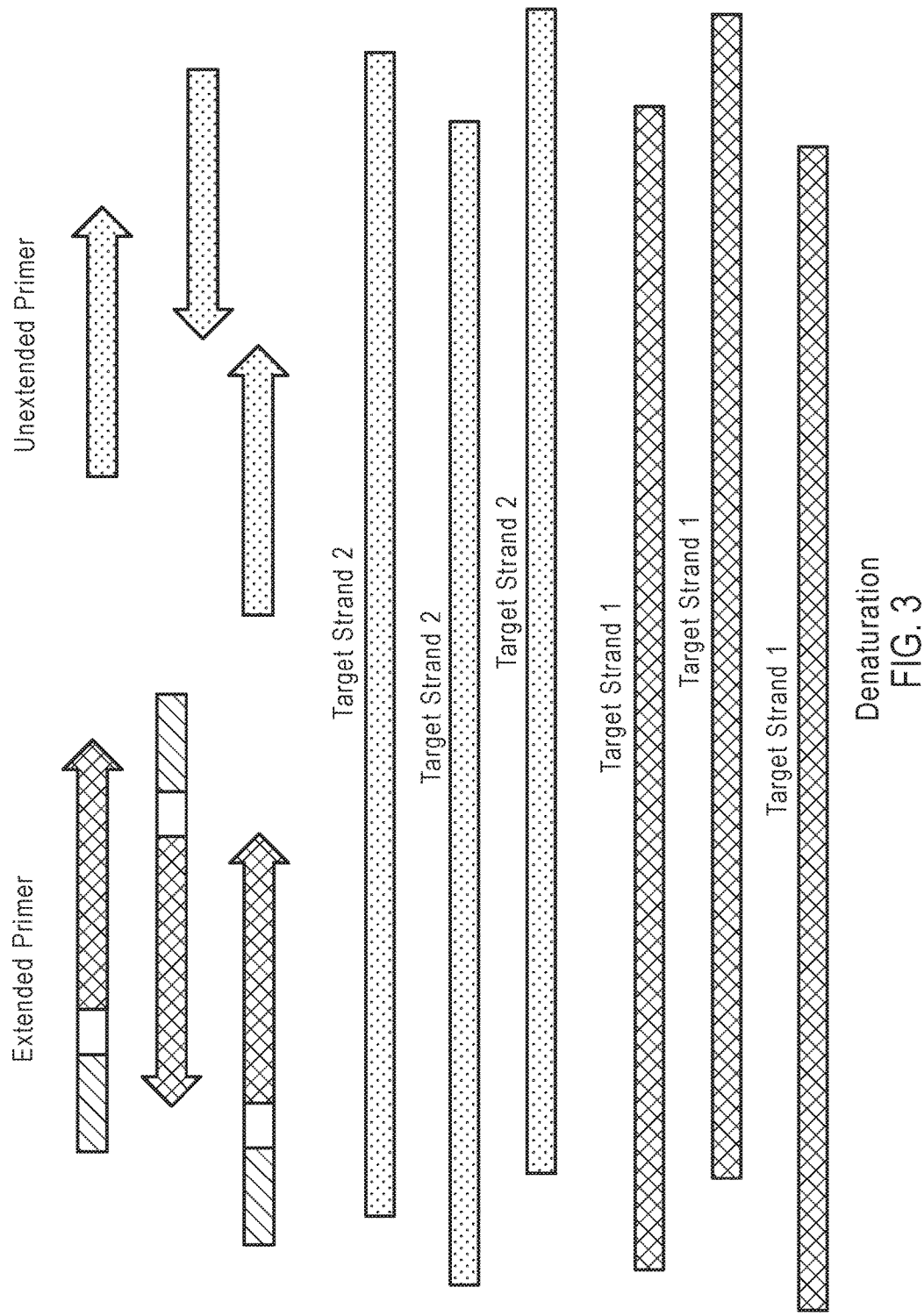
Figure 5A:
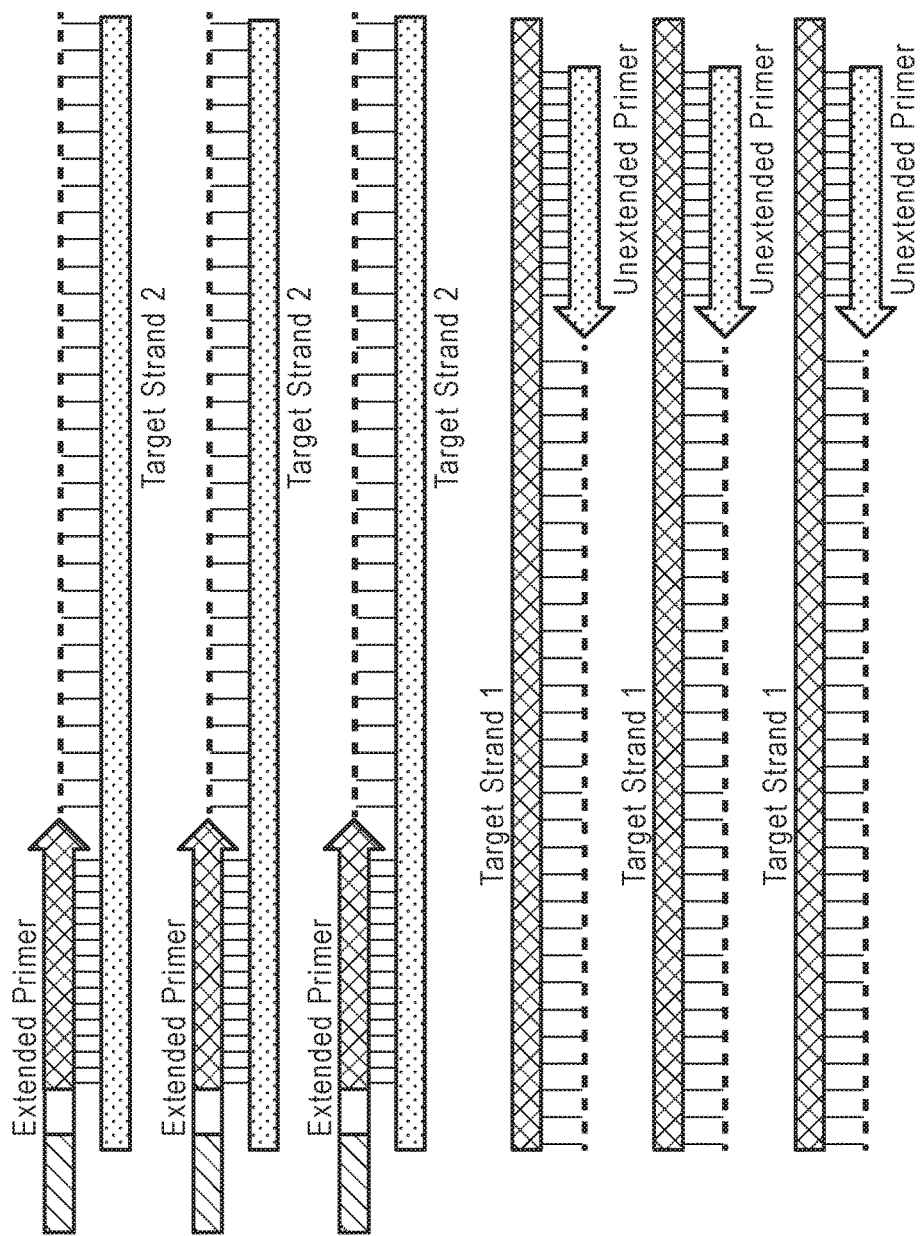
Figure 6:
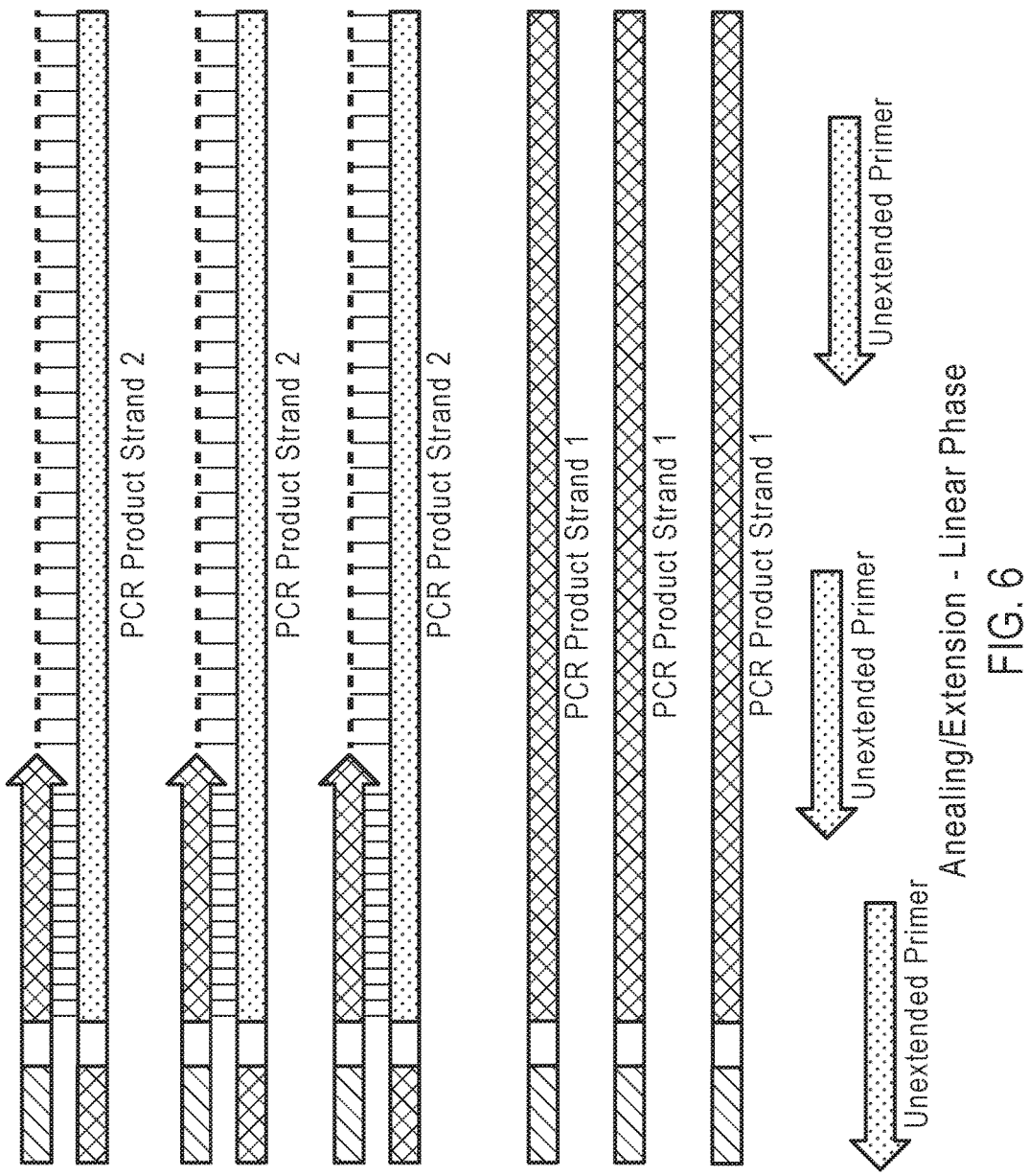

The sequence in the "B" region that is complementary to at least a portion of the "A" region can be a Direct Repeat or Inverted Repeat. Where the "B" region contains a Direct Repeat of a portion of the "A" region, different Extended Primer molecules can hybridize to one another intermolecularly, as shown in FIG. 2B. Where the "B" region contains an Inverted Repeat of a portion of the "A" region, Extended Primer molecules can hybridize intramolecularly, as shown in FIG. 2C, or to one another intermolecularly, as shown in FIG. 2A.

The portion of the "A" region to which a sequence in the "B" region is complementary is preferably at or near (e.g., within 1, 2, or 3 nucleotides from) the 5' end of the "A" region, i.e., at or near where the "A" region adjoins the "B" region (or the "C" region when a "C" region is present).

The "B" region of the Extended Primer is preferably 6 to 12 nucleotides in length, i.e., is preferably 6, 7, 8, 9, 10, 11 or 12 nucleotides in length. In specific embodiments, the "B" region of the Extended Primer is 8 to 10 nucleotides in length, i.e., is 8, 9 or 10 nucleotides in length.

The "C" region, when present in an Extended Primer, is preferably 1 to 6 nucleotides in length, i.e., is preferably 1, 2, 3, 4, 5, or 6 nucleotides in length.

The $T_m$ of the Extended Primer is preferably (but not necessarily) between approximately 68° C. and approximately 80° C. In particular embodiments, the $T_m$ of the Unextended Primer is between approximately 72° C. and approximately 78° C., for example approximately 72° C., approximately 73° C., approximately 74° C., approximately 75° C., approximately 76° C., approximately 77° C., or approximately 78° C.

The optional region "C" positioned between regions "A" and "B can act as a spacer between the "A" and "B" regions to allow the Extended Primer to form a hairpin loop and/or introduce a restriction endonuclease sequence (preferably a 6-cutter sequence) into the PCR product. The restriction endonuclease sequence can be within the "C" region in its entirety or be formed from all or a portion of the "C" region together with flanking 5' and/or 3' sequences from the "B" and "A" regions, respectively. To minimize interference with hybridization to the target nucleic acid, the "C" region is preferably not complementary to Target Strand 1 or Target Strand 2.

The $T_m$ of the Extended Primer is preferably at least approximately 6° C. greater than the $T_m$ of the Unextended Primer. Preferably, the Extended Primer has a $T_m$ that is at approximately 15° C. to 30° C. greater than the $T_m$ of the Unextended Primer.

The $T_m$ of the "A" region of the Extended Primer is preferably no more than approximately 3° C. higher or lower than the $T_m$ of the portion of the Unextended Primer (at least 75%) complementary to the target (exclusive of any 5' extensions), i.e., the $T_m$ of region in the forward primer that hybridizes to the target is preferably no more than approximately 3° C. higher or lower than the $T_m$ of the region in the reverse primer that that hybridizes to the target, and vice versa.

The "A" region of the Extended Primer is preferably at least 12 nucleotides in length, and preferably ranges from 12 to 30 nucleotides and more preferably from 14-25 nucleotides. In certain embodiments, the "A" region of the Extended Primer is 14, 15, 16, 17, 18, 19 or 20 nucleotides in length.

4.2.2. Unextended Primer

The Unextended Primer has a nucleotide sequence at least 75% sequence identity to a corresponding region in Target Strand 2. In certain embodiments, the Unextended Primer has a nucleotide sequence with at least 80%, at least 85%, at least 90%, or at least 95% sequence identity to the corresponding region in Target Strand 2. In yet other embodiments, the Unextended Primer has a nucleotide sequence with 100% sequence identity to the corresponding region of Target Strand 2.

Stated differently, in various embodiments Unextended Primer has a nucleotide sequence having least 75%, at least 80%, at least 85%, at least 90%, or at least 95% or 100% sequence identity to the complement of the corresponding 1 region in Target Strand 2. Typically, the more 5' any mismatches are between the primer sequence and the target sequence are positioned, the more likely they are to be tolerated during the PCR reaction. One of skill in the art can readily design primer sequences that have less than 100% sequence identity to the target strand but can still efficiently amplify target DNA.

The Unextended Primer may further have a 5' tail of 1, 2 or 3 nucleotides.

The $T_m$ of the Unextended Primer is preferably (but not necessarily) between approximately 50° C. and approximately 62° C. In particular embodiments, the $T_m$ of the Unextended Primer is between approximately 59° C. and approximately 62° C., for example approximately 59° C., approximately 60° C., approximately 61° C., or approximately 62° C.

The $T_m$ of the Unextended Primer is preferably at least approximately 6° C. lower than the $T_m$ of the Extended Primer. Preferably, the Unextended Primer has a $T_m$ that is at approximately 15° C. to 30° C. lower than the $T_m$ of the Extended Primer.

The $T_m$ of the region of the Unextended Primer (at least 75%) complementary to the target (exclusive of any 5' extensions) is preferably no more than approximately 3° C. higher or lower than the $T_m$ of the "A" region of the Extended Primer, i.e., the $T_m$ of region in the forward primer that hybridizes to the target is preferably no more than approximately 3° C. higher or lower than the $T_m$ of the region in the reverse primer that that hybridizes to the target, and vice versa.

The Unextended Primer is preferably at least 12 nucleotides in length, and preferably ranges from 12 to 30 nucleotides and more preferably from 14-25 nucleotides. In certain embodiments, the Unextended Primer is 14, 15, 16, 17, 18, 19 or 20 nucleotides in length.

4.2.3. Generic Primer

In some asymmetric PCR methods, for example as described in U.S. Pat. No. 8,735,067 B2, in addition to the forward and reverse primer pair a third, "generic" primer is used that has a sequence that is similar to a 5' oligonucleotide tail added to one of the primers. The generic primer is intended to participate in the amplification reaction after the initial PCR cycle to "balance" the amplification efficiency of different targets in a multiplex amplification reaction.

Without being bound by theory, the inventors believe that the inclusion of a generic primer as described in U.S. Pat. No. 8,735,067, which in the context of the present disclosure would have a sequence consisting essentially of the sequence of the "B" region of the Extended Primer (such generic primers referred to herein as "Generic Primers"), would reduce amplification efficiency using the Asymmetric Primer Pairs of the disclosure. Accordingly, the asymmetric DNA amplification methods of the disclosure are preferably performed in the absence of Generic Primers.

In a related embodiment, the asymmetric DNA amplification methods of the disclosure utilize a single Asymmetric Primer Pair per target region, i.e., do not include any additional primers, recognizing that an individual primer may be a mixture of primer molecule with closely related sequences resulting from the inclusion of mixed bases at certain positions in the primer. For clarity and avoidance of doubt, this embodiment does not preclude that use of a plurality of Asymmetric Primer Pairs in a multiplex amplification reaction, provided that a single Asymmetric Primer Pair is used for each amplicon.

4.3. Target Sequences and Sample Preparation

The PCR methods of the disclosure can be used to amplify nucleic acids from biological or environmental sources. The target molecules can be from cells and tissues of all taxonomic classes, including viruses, bacteria and eukaryotes, prokaryotes, protista, plants, fungi, and animals of all phyla and classes. The animals can be vertebrates, mammals, primates, and especially humans. Blood, serum, plasma, tissue, cells, saliva, sputum, urine, cerebrospinal fluid, pleural fluid, milk, tears, stool, sweat, semen, whole cells, cell constituent, and cell smears are suitable sources of target molecules.

In certain specific embodiments, the target nucleic acid molecules are from pathogens, e.g., bacteria, viruses or fungi, that can be found in human blood, urine or peritoneal fluid. Examples of such pathogens include, but are not limited to, *Mycobacterium tuberculosis, Mycobacterium avium* subsp *paratuberculosis, Staphylococcus aureus* (including methicillin sensitive and methicillin resistant *Staphylococcus aureus* (MRSA)), *Streptococcus pyogenes, Streptococcus pneumoniae, Streptococcus agalactiae, Haemophilus influenzae, Haemophilus parainfuluezae, Moraxella catarrhalis, Klebsiella pneumoniae, Escherichia coli, Pseudomonas aeruginosa, Acinetobacter* sp., *Bordetella pertussis, Neisseria meningitidis, Bacillus anthracis, Nocardia* sp., *Actinomyces* sp., *Mycoplasma pneumoniae, Chlamydia pneumonia, Legionella* species, *Pneumocystis jiroveci*, influenza A virus, cytomegalovirus, rhinovirus, *Enterococcus faecium, Acinetobacter baumannii, Corynebacterium amycolatum, Enterobacter aerogenes, Enterococcus faecalis* CI 4413, *Serratia marcescens, Streptococcus equi*, and *Candida albicans*.

The target nucleic acid molecules are preferably DNA but can also be RNA. In the case of RNA templates, the PCR reaction can be preceded by a reverse transcription reaction to generate cDNA molecules for use as target molecules in the PCR reaction. The reverse transcription reaction can be performed in the same reaction mixture or in a separate reaction mixture from the PCR reaction. Methods of reverse transcription are well known in the art.

The target nucleic acid molecules can be reverse transcribed (if RNA), extracted and/or purified from biological or environmental samples prior to incorporation into the initial PCR mixture.

In some embodiments, the target nucleic acid molecules are extracted by a bead beating process as described in U.S. Patent Publication No. 20170218356, the contents of which are incorporated by reference herein in its entirety.

4.4. PCR Reaction 4.4.1. The Initial Reaction Mixture

The initial PCR reaction mixture includes:
Nucleic acid sample;
Asymmetric Primer Pair;
Thermostable DNA polymerase; and
PCR Reagents.

Nucleic Acid Sample:

The sample nucleic acid may include a biological sample or environmental sample or a sample derived therefrom, e.g., DNA extracted or purified therefrom. The biological sample can be, for example, blood, serum, plasma, tissue, cells, saliva, sputum, urine, cerebrospinal fluid, pleural fluid, milk, tears, stool, sweat, semen, whole cells, cell constituent, cell smear, or an extract or derivative thereof. The sample nucleic acid may also be a positive or negative control sample. A negative control nucleic acid sample can contain no nucleic acid or a nucleic acid containing known not to contain sequences to which the Asymmetric Primer Pair hybridizes.

Asymmetric Primer Pair:

The initial concentration of the Extended Primer and the Unextended Primer in the PCR reaction can each range from 200 nM to 6 µM. The Extended Primer and Unextended Primer can be included in equimolar quantities in the initial PCR reaction, e.g., at concentrations ranging between about 200 nM and 1 µM each, for instance at concentrations of 500 nM each. Alternatively, the Extended Primer and Unextended Primer can be included in non-equimolar quantities in the initial PCR reaction. In certain embodiments, the initial concentration of the Extended Primer is preferably in an excess of the concentration of Unextended Primer, for example about a 2-fold to 30-fold molar excess. Accordingly, in certain aspects, the concentration the Extended Primer ranges between about 1 µM and 6 µM and the concentration of the Unextended Primer ranges between about 50 nM and 200 nM.

The Asymmetric Primer Pair can be designed to amplify nucleic acid from any source, and for diagnostic applications the Asymmetric Primer Pair can be design to amplify DNA from pathogens such as those identified in Section 4.3.

The Asymmetric Primer Pair can be designed so as to be capable of amplifying conserved nucleic acid sequences present in many species simultaneously, for example the highly conserved 16S ribosomal sequence in bacteria.

Thermostable DNA Polymerase:

The thermostable polymerases that can be used in the asymmetric PCR reactions of the disclosure includes, but are not limited to, Vent (Tli/*Thermoccus Literalis*), Vent exo-, Deep Vent, Deep Vent exo-, Taq (*Thermus aquaticus*), Hot Start Taq, Hot Start Ex Taq, Hot Start LA Taq, DreamTaq™ TopTaq, RedTaq, Taqurate, NovaTaq™ SuperTaq™, Stoffel Fragment, Discoverase™ dHPLC, 9° Nm, Phusion®, LongAmp Taq, LongAmp Hot Start Taq, OneTaq, Phusion® Hot Start Flex, Crimson Taq, Hemo KlenTaq, KlenTaq, Phire Hot Start II, DyNAzyme I, DyNAzyme II, M-MuIV Reverse Transcript, PyroPhage®, Tth (Thermos termophilus HB-8), Tfl, Amlitherm™ *Bacillus* DNA, DisplaceAce™ Pfu (*Pyrococcus furiosus*), Pfu Turbot, Pfunds, ReproFast, PyroBest™, VeraSeq, Mako, Manta, Pwo (*pyrococcus, woesei*), ExactRun, KOD (*thermococcus kodakkaraensis*), Pfx, ReproHot, Sac (*Sulfolobus acidocaldarius*), Sso (*Sulfolobus solfataricus*), Tru (*Thermus ruber*, Pfx50™ (*Thermococcus zilligi*), AccuPrime™ GC-Rich (*Pyrolobus fumarius*), *Pyrococcus* species GB-D, Tfi (*Thermus filiformis*), Tfi exo-, ThermalAce™ Tac (*Thermoplasma acidophilum*), (Mth (*M. thermoautotrophicum*), Pab (*Pyrococcus abyssi*), Pho (*Pyrococcus horikosihi*, B103 (Picovirinae Bacteriophage B103), Bst (*Bacillus stearothermophilus*), Bst Large Fragment, Bst 2.0, Bst 2.0 WarmStart, Bsu, Terminator™, Terminator™ II, Terminator™ III, and Terminator™ T. In a preferred embodiment, the DNA polymerase is a Taq polymerase, such as Taq, Hot Start Taq, Hot Start Ex Taq, Hot Start LA Taq, DreamTaq™ TopTaq, RedTaq, Taqurate, NovaTaq™ or SuperTaq™

PCR Reagents:

The PCR Reagents (dNTP's, buffering agent, salt) are well known to the skilled artisan. They can be added separately to the initial PCR reaction mixture or premixed in whole or in part, for example as part of as a PCR master mix.

Conveniently, a PCR master mix can be prepared in advance of initiating the reaction and stored for use. The PCR master mix can include the DNA polymerase, dNTPs (including the optional fluorescently labeled dNTPs where desired), buffering agent and/or salt, and optionally, a reverse transcriptase and various additives such as a preservative. The primers and sample nucleic acid are typically not incorporated into the PCR master mix, but incorporated into the initial PCR reaction mixture shortly prior to initiating the PCR reaction.

The methods of the disclosure further include the optional step of forming the initial reaction mixture prior to initiating thermal cycling, by combining the components of the initial reaction mixture in a PCR vessel, such as a PCR tube.

4.4.2. The PCR Reaction Conditions

An illustrative set of asymmetric cycles for use in the asymmetric PCR methods of the disclosure is shown in Table 2.

number of cycles will depend on the copy number of the target DNA in the initial PCR mixture: the greater the initial copy number the fewer number of cycles are needed in the exponential phase to produce a sufficient quantity of PCR products to serve as templates for the linear phase. The optimization of cycle number is routine for the skilled artisan.

The temperatures shown in Table 2 are particularly useful where the $T_m$ of the Extended Primer is greater than 72° C. (e.g., 75-80° C.) and the $T_m$ of the Unextended Primer is above 58° C. but below 72° C. (e.g., 60-62° C.) and when the thermostable DNA polymerase is active at 72° C.

The cycle times, particularly the extension times, can be varied according to the melting temperatures of the primers and the length of the PCR product, with longer PCR products calling for longer extension times. A rule of thumb is that the extension step should be at least 60 seconds per 1,000 bases of amplicon. The extension step can be extended in the linear phase to provide additional time for annealing.

4.5. Detection of PCR Products

PCR Product Strand 2, which is the enriched single stranded PCR product produced by the methods described herein, can be labeled with fluorescent labels for detection.

Fluorescent labeling can be achieved by fluorescently labeled nucleotide incorporation during PCR and/or by the use of labeled primers for PCR.

Examples of suitable fluorescent moieties include FITC, EDANS, Texas red, 6-joe, TMR, Alexa 488, Alexa 532, "BODIPY FL/C3", "BODIPY R6G", "BODIPY FL", Alexa 532, "BODIPY FL/C6", "BODIPY TMR", 5-FAM, "BODIPY 493/503", "BODIPY 564", "BODIPY 581", Cy3, Cy5, R110, TAMRA, Texas red, and x-Rhodamine.

Fluorescent moieties can be attached to dNTPs, particularly those containing cytosine as a base (cytidylic acid, cytidine 5'-phosphate, cytidine 5'-diphosphate, cytidine 5'-triphosphate, or a polymer thereof, or a polymer containing cytidylic acid).

The position of the dNTP labeling can be at the base (amino group), phosphate group (OH group), or deoxyribose moiety (2'- or 3'-OH group). The preferred position is either at the base.

Like other nucleotides, fluorescently labeled dNTPs can be incorporated into both strands of a PCR amplicon at random sites, typically dC sites, and extended by DNA polymerase.

TABLE 2

| Phase | Step | Temperature | Time | No. of Cycles |
|---|---|---|---|---|
| Initial denaturation | Initial denaturation | 90-100° C., preferably 95° C. | 0-5 minutes, preferably 2 minutes | 0-1 |
| Exponential phase | Denaturation | 90-100° C., preferably 95° C. | 15-25 seconds, preferably 20 seconds | 20-40, preferably 30-37 (e.g., 35) |
|  | Annealing | 58° C. | 12-18 seconds, preferably 15 seconds |  |
|  | Extension | 72° C. | 30-50 seconds, preferably 40 seconds |  |
| Linear phase | Denaturation | 90-100° C., preferably 95° C. | 15-25 seconds, preferably 20 seconds | 15-25, preferably 20 |
|  | Simultaneous annealing and extension | 72° C. | 40-60 seconds, preferably 50 seconds |  |
| Extended extension | Extended extension | 72° C. | 0-5 minutes, preferably 2 minutes | 0-1 |

The ranges of numbers of cycles shown in Table 2 can be used for any Asymmetric Primer Pair, and the optimal Fluorescent dNTPs are commercially available in highly concentrated form and can be added to the PCR reaction mixture without adjusting the concentration of each unlabeled dNTP. For most PCR amplifications, the typical ratio of dNTP to fluorescent dNTPs is between 100:1 and 1000:1. Thus, to fluorescently labeled dNTPs can be included among the PCR Reagents at 0.1% to 1% the (molar) quantity of the unlabeled dNTPs.

Detection of fluorescently labeled PCR products (e.g., the single stranded Product Strand 2 that is produced in excess in the methods of the disclosure) can be achieved through hybridization to probe molecules, for example probe molecules bound to a microarray. A suitable microarray system takes advantage of three-dimensional crosslinked polymer networks, as described in U.S. Pat. No. 9,738,926, the contents of which are incorporated by reference herein in their entireties.

4.6. KITS

The present disclosure further provides kits suitable for carrying out the asymmetric PCR methods describe herein. The kits typically include at least an Asymmetric Primer Pair. Additionally, kits of the disclosure can include probe molecules, a DNA polymerase, unlabeled dNTP's, labeled dNTPs, buffers, salt solutions, or any combination thereof. Some of the reagents (e.g., the DNA polymerase, dNTPs, salt and/or buffer) can be pre-combined in the form of a master mix.

5. EXAMPLES

An initial PCR reaction was created with an Asymmetric Primer Pair designed to amplify a 506-bp region from the *S. aureus* 16S gene (not including primer sequences) using an Extended Primer for the forward primer and an Unextended Primer for the reverse primer. The nucleic acid sample was human DNA spiked with a known copy number of *S. aureus* genomic DNA (the target DNA for these studies). The forward primer (with a calculated Tm of 68.1° C.) was labeled with Cy5 at the 5-prime end and contained an "A" region (with a calculated Tm of 64.09° C.), a "B" region complementary to the 5' end of the "A" region, and no "C" region as a spacer between the "A" and "B" regions. The reverse primer included an inosine which could base pair with any other base in the target sequence. Depending on the complementary target base, the Tm of the reverse primer ranged from 60-61.9° C. The initial PCR reaction was subjected to the following PCR cycle:

an initial denaturation period of 2 minutes at 95° C.,
exponential cycles each consisting of 20 s denaturation at 95° C., 15 s annealing at 58° C., and 40 s extension at 72° C.;
linear cycles each consisting of 20 s denaturation at 95° C. and then simultaneous annealing/extension at 72° C., and
finally a 2-minute extended extension period at 72° C.

In Experiment 1, the numbers of target DNA molecules and exponential and linear cycles was varied to optimize the numbers of exponential and linear cycles for the copy number of target nucleic acid. The amount of reverse (Unextended Primer) included was determined so that the Unextended Primer would be exhausted or nearly exhausted by the end of the exponential phase and very few molecules of Unextended Primer would remain by the linear phase of the asymmetric PCR. The results of these calculations are shown in Table 3:

TABLE 3

| | | | Reverse Primer Required no. of cycles to use up primer completely | | |
|---|---|---|---|---|---|
| Reverse Primer concentration | Reverse Primer molecules/L | Reverse Primer molecules in 20 µl reaction | 1 genomic copy | 10 genomic copies | 100 genomic copies |
| 0.1 | $6.02^{+16}$ | $1.20^{+12}$ | 40.1 | 36.8 | 33.5 |
| 0.2 | $1.20^{+17}$ | $2.41^{+12}$ | 41.1 | 37.8 | 34.5 |
| 0.5 | $3.01^{+17}$ | $6.02^{+12}$ | 42.4 | 39.1 | 35.8 |

Figure 8:
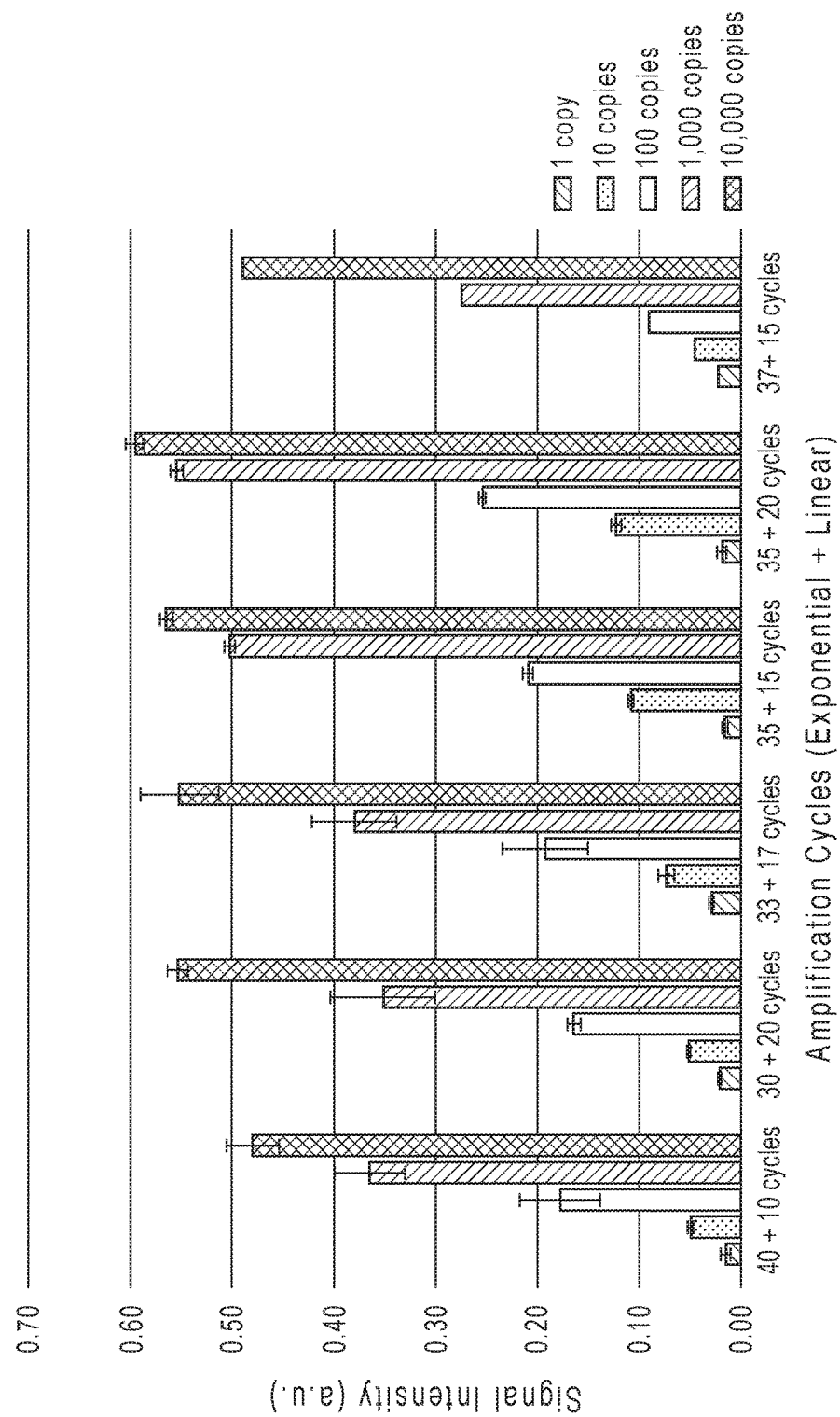
FIG. 8 shows the results of a study to optimize the number of exponential and linear cycles in the asymmetric PCR methods of the disclosure using *S. aureus* primers and probes. The signal intensity is measured in arbitrary units ("a.u.").

The amount of PCR product produced in Experiment 1 was quantified by hybridization to a microarray. The results are shown in FIG. 8.

In Experiment 2, the quantity of PCR product produced from different template concentrations using asymmetric PCR and symmetric PCR was compared, using 500 nM of each of the forward and reverse probes in the PCR reaction. For the asymmetric reaction, the numbers of exponential and linear cycles used were 35 and 20, respectively. In the symmetric reaction, no linear cycles were used.

Figure 9:
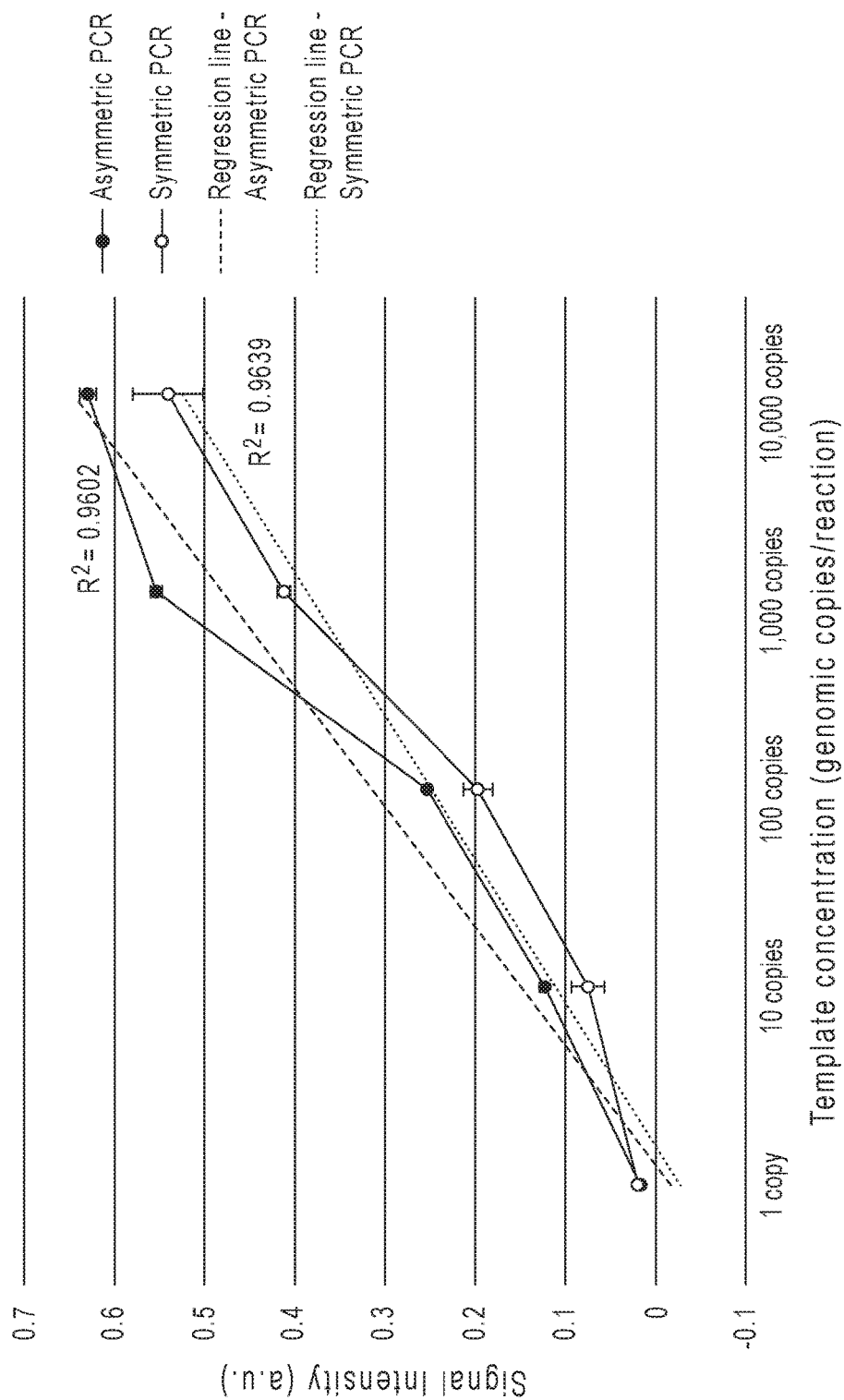
FIG. 9 shows the results of a study to compare the detection limit of low copy number targets via the asymmetric PCR methods of the disclosure vs. traditional (symmetric) PCR using *S. aureus* primers and probes. The signal intensity is measured in arbitrary units ("a.u.").

The amount of PCR product was detected by hybridization to a microarray. The results are shown in FIG. 9. The $R^2$ value of greater than 0.95 indicates that in each case the regression line is a valid fit for the data.

6. SPECIFIC EMBODIMENTS

The present disclosure is exemplified by the specific embodiments below.

1. A method for production of single stranded DNA amplicons via an asymmetric polymerase chain reaction (PCR), comprising the steps of:
   (a) subjecting an initial mixture to a first phase of thermal cycling under amplifying PCR conditions, said initial mixture comprising:
   (i) a nucleic acid sample;
   (ii) an Asymmetric Primer Pair,
   (iii) a thermostable DNA polymerase, and
   (iv) PCR Reagents,
   wherein the first phase of thermal cycling comprises cycling through at least three temperatures, said three temperatures comprising: (1) a first temperature above the $T_m$ of a target nucleic acid for denaturation, (2) a second temperature below the $T_m$ of the Unextended Primer for primer annealing, and (3) a third temperature suitable for extension by the thermostable DNA polymerase,
   thereby producing an intermediate mixture, said intermediate mixture comprising DNA amplicons extended from both the Unextended Primer and the Extended Primer if the target nucleic acid is present in the sample;
   (b) subjecting the intermediate mixture to second phase of thermal cycling, said second phase of comprising cycling through: (1) a fourth temperature above the $T_m$ of the DNA amplicons for denaturation, (2) a fifth temperature that is (i) below the $T_m$ of the Extended Primer, (ii) above the $T_m$ of the Unextended Primer and (iii) suitable for extension by the thermostable DNA polymerase, thereby producing a final mixture, said final mixture comprising single stranded DNA amplicons if the target nucleic acid is present in the sample.

2. The method of embodiment 1, wherein step (a) is preceded by an initial denaturation period.

3. The method of embodiment 2, wherein the initial denaturation is carried out at the first temperature.

4. The method of any one of embodiments 1 to 3, wherein step (b) is followed by an additional extension period.

5. The method of embodiment 4, wherein the additional extension is carried out at the fifth temperature.

6. The method of any one of embodiments 1 to 5, wherein the first and fourth temperatures are the same.

7. The method of any one of embodiments 1 to 6, wherein the third and fifth temperatures are the same.

8. The method of any one of embodiments 1 to 7, wherein the "B" region of the Extended Primer is the complement of an inverted repeat of at least a portion of the "A" region.

9. The method of embodiment 8, wherein the "B" region is at least 4 nucleotides in length.

10. The method of embodiment 8 or embodiment 9, wherein the "B" region is 3 nucleotides shorter than the "A" region.

11. The method of any one of embodiments 1 to 7, wherein the "B" region of the Extended Primer is the complement of a direct repeat of at least a portion of the "A" region.

12. The method of embodiment 11, wherein the "B" region of the Extended Primer is at least 4 nucleotides in length.

13. The method of embodiment 11 or embodiment 12, wherein the "B" region of the Extended Primer is 3 nucleotides shorter than the "A" region.

14. The method of any one of embodiments 1 to 11, wherein the "B" region of the Extended Primer is 7 to 15 nucleotides in length.

15. The method of embodiment 14, wherein the "B" region of the Extended Primer is 6 to 12 nucleotides in length.

16. The method of embodiment 15, wherein the "B" region of the Extended Primer is 8 to 10 nucleotides in length.

17. The method of embodiment 15, wherein the "B" region of the Extended Primer is 6 nucleotides in length.

18. The method of embodiment 15, wherein the "B" region of the Extended Primer is 7 nucleotides in length.

19. The method of embodiment 15, wherein the "B" region of the Extended Primer is 8 nucleotides in length.

20. The method of embodiment 15, wherein the "B" region of the Extended Primer is 9 nucleotides in length.

21. The method of embodiment 15, wherein the "B" region of the Extended Primer is 10 nucleotides in length.

22. The method of embodiment 15, wherein the "B" region of the Extended Primer is 11 nucleotides in length.

23. The method of embodiment 15, wherein the "B" region of the Extended Primer is 12 nucleotides in length.

24. The method of any one of embodiments 1 to 23, wherein the Unextended Primer does not have a 5' tail extension.

25. The method of any one of embodiments 1 to 23, wherein the Unextended Primer has a 5' tail extension of 3 nucleotides or less.

26. The method of any one of embodiments 1 to 25, wherein the Unextended Primer is 12 to 35 nucleotides in length.

27. The method of embodiment 26, wherein the Unextended Primer is 15 to 25 nucleotides in length.

28. The method of embodiment 26, wherein the Unextended Primer is 18 to 20 nucleotides in length.

29. The method of any one of embodiments 1 to 28, wherein the "A" region of the Extended Primer is 12 to 35 nucleotides in length.

30. The method of embodiment 29, wherein the "A" region of the Extended Primer is 15 to 25 nucleotides in length.

31. The method of embodiment 29, wherein the "A" region of the Extended Primer is 18 to 20 nucleotides in length.

32. The method of any one of embodiments 1 to 31, wherein the Extended Primer comprises a "C" region.

33. The method of embodiment 32, wherein the "C" region is 1-8 nucleotides in length.

34. The method of embodiment 32 or embodiment 33, wherein the "C" region, alone or in combination with the flanking "A" and/or "B" region nucleotides, forms a recognition site for a restriction endonuclease.

35. The method of embodiment 34, wherein the restriction endonuclease is a 6-cutter.

36. The method of any one of embodiments 1 to 35, wherein the $T_m$ of the Extended Primer is greater than the $T_m$ of the Unextended Primer by at least 8° C.

37. The method of embodiment 36, wherein the $T_m$ of the Extended Primer is greater than the $T_m$ of the Unextended Primer by 10° C. to 30° C.

38. The method of embodiment 37, wherein the $T_m$ of the Extended Primer is greater than the $T_m$ of the Unextended Primer by 15° C. to 30° C. 39. The method of embodiment 38, wherein the $T_m$ of the Extended Primer is greater than the $T_m$ of the Unextended Primer by 12° C. to 20° C.

40. The method of embodiment 39, wherein the $T_m$ of the Extended Primer is greater than the $T_m$ of the Unextended Primer by 13° C. to 17° C.

41. The method of any one of embodiments 1 to 40, wherein the $T_m$ of the Extended Primer ranges between 68° C. and 80° C.

42. The method of embodiment 41, wherein the $T_m$ of the Extended Primer is between 73° C. and 77° C.

43. The method of embodiment 42, wherein the $T_m$ of the Extended Primer is 75° C.

44. The method of any one of embodiments 1 to 43, wherein the $T_m$ of the Unextended Primer ranges between 50° C. and 62° C.

45. The method of embodiment 44, wherein the $T_m$ of the Unextended Primer is between 58° C. and 62° C.

46. The method of embodiment 45, wherein the $T_m$ of the Unextended Primer is 60° C.

47. The method of any one of embodiments 1 to 46, wherein the $T_m$ of the "A" region of the Extended Primer ranges between 50° C. and 62° C.

48. The method of embodiment 47, wherein the $T_m$ of the "A" region of the Extended Primer is between 58° C. and 62° C.

49. The method of embodiment 48, wherein the $T_m$ of the "A" region of the Extended Primer is 60° C.

50. The method of any one of embodiments 1 to 49, wherein the $T_m$ of the "A" region of the Extended Primer and the $T_m$ of the Unextended Primer vary by no more than 3° C.

51. The method of any one of embodiments 1 to 50, wherein the first temperature is 95° C.

52. The method of any one of embodiments 1 to 51, wherein the second temperature is 58° C.

53. The method of any one of embodiments 1 to 52, wherein the third temperature is 72° C.

54. The method of any one of embodiments 1 to 53, wherein the fourth temperature is 95° C.

55. The method of any one of embodiments 1 to 54, wherein the fifth temperature is 72° C.

56. The method of any one of embodiments 1 to 55, wherein the DNA amplicons extended from both the Unextended Primer and the Extended Primer in the intermediate mixture are hybridized to one another to form double stranded DNA amplicons.

57. The method of any one of embodiments 1 to 56, wherein the DNA amplicons produced by the PCR reaction range from 100 to 2,500 nucleotides in length.

58. The method of embodiment 57, wherein the DNA amplicons produced by the PCR reaction range from 200 to 2,000 nucleotides in length.

59. The method of embodiment 57, wherein the DNA amplicons produced by the PCR reaction range from 250 to 1,500 nucleotides in length.

60. The method of embodiment 57, wherein the DNA amplicons produced by the PCR reaction range from 300 to 1,000 nucleotides in length.

61. The method of any one of embodiments 1 to 60, wherein the nucleic acid sample is a test nucleic acid sample.

62. The method of embodiment 61, wherein the test nucleic acid sample contains or is at risk of containing or is suspected of containing target nucleic acid molecules.

63. The method of any one of embodiments 1 to 60, wherein the nucleic acid sample is a control nucleic acid sample.

64. The method of embodiment 63, wherein the control nucleic acid sample is a positive control sample known to contain target nucleic acid molecule(s).

65. The method of embodiment 63, wherein the control nucleic acid sample is a positive control sample known to contain target nucleic acid molecules.

66. The method of any one of embodiments 1 to 65, which is a multiplex PCR reaction.

67. The method of embodiment 66, wherein the initial mixture comprises at least two Asymmetric Primer Pairs.

68. The method of embodiment 67, wherein the initial mixture comprises at two, three or four Asymmetric Primer Pairs.

69. The method of any one of embodiments 61 to 68, wherein the initial mixture further comprises control primers.

70. The method of embodiment 69, wherein the control primers are complementary to a target sequence that is different from the target sequence(s) to which the Asymmetric Primer Pair(s) are complementary.

71. The method of embodiment 69 or embodiment 70, wherein the control primers are standard primers.

72. The method of embodiment 69 or embodiment 70, wherein the control primers are an Asymmetric Primer Pair.

73. The method of any one of embodiments 1 to 72, wherein the PCR is performed in the absence of a Generic Primer.

74. The method of any one of embodiments 1 to 73, wherein the first phase comprises 20-40 rounds of thermal cycling.

75. The method of embodiment 74, wherein the second phase comprises 30-37 rounds of thermal cycling.

76. The method of any one of embodiments 1 to 75, wherein the first phase results in exponential amplification of both strands of the target nucleic acid.

77. The method of any one of embodiments 1 to 76, wherein the second phase comprises 15-25 rounds of thermal cycling.

78. The method of any one of embodiments 1 to 77, wherein the second phase results in linear amplification of a single strand of the target nucleic acid.

79. The method of any one of embodiments 1 to 78, wherein the concentration of each of the Extended Primer and the Unextended Primer in the initial mixture ranges between 200 nM to 6 µM.

80. The method of any one of embodiments 1 to 79, wherein the concentration of each of the Extended Primer and the Unextended Primer in the initial mixture is the same.

81. The method of embodiment 80, wherein the concentration of each of the Extended Primer and the Unextended Primer in the initial mixture ranges between 100 nM and 1000 nM.

82. The method of embodiment 81, wherein the concentration of each of the Extended Primer and the Unextended Primer in the initial mixture ranges between 250 nM and 750 nM.

83. The method of embodiment 82, wherein the concentration of each of the Extended Primer and the Unextended Primer in the initial mixture is approximately 500 nM.

84. The method of any one of embodiments 1 to 79, wherein the concentrations of the Extended Primer and the Unextended Primer in the initial mixture are different.

85. The method of embodiment 84, wherein the concentration of the Extended Primer in the initial mixture ranges between 1 µM and 6 µM.

86. The method of embodiment 84 or embodiment 85, wherein the concentration of the Unextended Primer in the initial mixture ranges between 50 nM and 200 nM.

87. The method of any one of embodiments 1 to 86, wherein the Extended Primer is labeled.

88. The method of embodiment 87, wherein the Extended Primer is labeled at its 5' end.

89. The method of embodiment 87 or embodiment 88, wherein the label is a fluorophore.

90. The method of any one of embodiments 1 to 89, wherein the Asymmetric Primer Pair comprises sequences complementary to bacterial sequences.

91. The method of embodiment 90, wherein the bacterial sequences are 16S DNA sequences.

92. The method of embodiment 90, wherein the bacterial sequences are bacterial internal transcribed region DNA sequences.

93. The method of any one of embodiments 1 to 89, wherein the Asymmetric Primer Pair comprises sequences complementary to fungal DNA sequences.

94. The method of any one of embodiments 1 to 93, wherein the sample is a biological sample.

95. The method of embodiment 94, wherein the biological sample is blood or a sample processed, extracted or fractionated therefrom.

96. The method of embodiment 94, wherein the biological sample is peritoneal dialysis fluid or a sample processed, extracted or fractionated therefrom.

97. The method of embodiment 94, wherein the biological sample is urine or a sample processed, extracted or fractionated therefrom.

98. The method of embodiment 94, wherein the biological sample is sputum or a sample processed, extracted or fractionated therefrom.

99. The method of embodiment 94, wherein the biological sample is a wound swab or a sample processed, extracted or fractionated therefrom.

100. The method of any one of embodiments 1 to 93, wherein the sample is an environmental sample.

101. The method of any one of embodiments 1 to 100, which further comprises detecting the single stranded PCR amplicon.

102. The method of embodiment 101, which comprises hybridizing the single stranded PCR amplicon to a probe molecule and detecting hybridization of the amplicon to the probe molecule.

103. The method of embodiment 102, wherein the probe molecule is labeled.

104. The method of embodiment 103, wherein the probe molecule is labeled with a fluorophore.

105. The method of any one of embodiments 102 to 104, wherein the probe molecule is complementary to at least a portion of the Extended Primer.

106. The method of embodiment 105, wherein the probe molecule is at least 15 nucleotides in length.

107. The method of embodiment 105 or embodiment 106, wherein the probe molecule has a region of complementarity to at least 8 nucleotides of the "A" region of the Extended Primer.

108. The method of any one of embodiments 102 to 104, wherein the probe molecule is complementary to at least a portion of the Unextended Primer.

109. The method of embodiment 108, wherein the probe molecule is at least 15 nucleotides in length.

110. The method of embodiment 108 or embodiment 109, wherein the probe molecule has a region of complementarity to at least 8 nucleotides of the "A" region of the Extended Primer.

While various specific embodiments have been illustrated and described, it will be appreciated that various changes can be made without departing from the spirit and scope of the disclosure(s).

7. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A method for production of single stranded DNA amplicons via an asymmetric polymerase chain reaction (PCR), comprising the steps of:
   (a) subjecting an initial mixture to a first phase of thermal cycling under amplifying PCR conditions, said initial mixture comprising:
      (i) a nucleic acid sample;
      (ii) an Asymmetric Primer Pair,
      (iii) a thermostable DNA polymerase, and
      (iv) PCR Reagents,
   wherein the first phase of thermal cycling comprises cycling through at least three temperatures, said three temperatures comprising: (1) a first temperature above the $T_m$ of the target nucleic acid for denaturation, (2) a second temperature below the $T_m$ of the Unextended Primer for primer annealing, and (3) a third temperature suitable for extension by the thermostable DNA polymerase,
   thereby, producing an intermediate mixture, said intermediate mixture comprising double stranded DNA amplicons extended from both the Unextended Primer and the Extended Primer if the target nucleic acid is present in the sample;
   (b) subjecting the intermediate mixture to a second phase of thermal cycling, said second phase of thermal cycling comprising cycling through: (1) a fourth temperature above the $T_m$ of the double stranded DNA amplicons for denaturation, (2) a fifth temperature that is (i) below the $T_m$ of the Extended Primer, (ii) above the $T_m$ of the Unextended Primer and (iii) suitable for extension by the thermostable DNA polymerase,
   thereby producing a final mixture, said final mixture comprising single stranded DNA amplicons if the target nucleic acid is present in the sample;
   wherein the asymmetric PCR is performed in the absence of a Generic Primer.

2. The method of claim 1, wherein step (a) is preceded by an initial denaturation period.

3. The method of claim 2, wherein the initial denaturation is carried out at the first temperature.

4. The method of claim 1, wherein step (b) is followed by an additional extension period.

5. The method of claim 4, wherein the additional extension is carried out at the fifth temperature.

6. The method of claim 1, wherein the first and fourth temperatures are the same and/or the third and fifth temperatures are the same.

7. The method of claim 1, wherein the "B" region of the Extended Primer is Inverted Repeat of at least a portion of the "A" region.

8. The method of claim 1, wherein the Unextended Primer does not have a 5' tail extension.

9. The method of claim 1, wherein the Extended Primer comprises a "C" region.

10. The method of claim 9, wherein the "C" region alone forms a recognition site for a restriction endonuclease.

11. The method of claim 9, wherein the "C" region, in combination with the flanking "A" and/or "B" region nucleotides, forms a recognition site for a restriction endonuclease.

12. The method of claim 1, wherein the $T_m$ of the Extended Primer is greater than the $T_m$ of the Unextended Primer by at least 8° C.

13. The method of claim 1, wherein the $T_m$ of the "A" region of the Extended Primer and the $T_m$ of the Unextended Primer vary by no more than 3° C.

14. The method of claim 1, wherein
(a) the first temperature is 95° C.;
(b) the second temperature is 58° C.;
(c) the third temperature is 72° C.;
(d) the fourth temperature is 95° C.;
(e) the fifth temperature is 72° C.; or
(f) any combination of (a)-(e).

15. The method of claim 1, wherein the nucleic acid sample is a test nucleic acid sample.

16. The method of claim 1, wherein the nucleic acid sample is a control nucleic acid sample.

17. The method of claim 1, which is a multiplex PCR reaction.

18. The method of claim 1, wherein the first phase results in exponential amplification of both strands of the target nucleic acid and/or the second phase results in linear amplification of a single strand of the target nucleic acid.

19. The method of claim 1, wherein the Asymmetric Primer Pair comprises sequences complementary to bacterial sequences or fungal DNA sequences.

20. The method of claim 1, wherein the sample is a biological sample.

21. The method of claim 20, wherein the biological sample is blood or a sample processed, extracted or fractionated therefrom.

22. The method of claim 20, wherein the biological sample is peritoneal dialysis fluid or a sample processed, extracted or fractionated therefrom.

23. The method of claim 20, wherein the biological sample is urine or a sample processed, extracted or fractionated therefrom.

24. The method of claim 20, wherein the biological sample is sputum or a sample processed, extracted or fractionated therefrom.

25. The method of claim 20, wherein the biological sample is a wound swab or a sample processed, extracted or fractionated therefrom.

26. The method of claim 1, wherein the sample is an environmental sample.

27. The method of claim 1, which further comprises detecting the single stranded PCR amplicon.

28. The method of claim 1, wherein the Unextended Primer has a 5' tail extension of 3 nucleotides or less.

29. The method of claim 1, wherein the "B" region of the Extended Primer is a Direct Repeat of at least a portion of the "A" region.

* * * * *